(12) United States Patent
Bikovsky et al.

(10) Patent No.: US 6,891,136 B2
(45) Date of Patent: May 10, 2005

(54) ELECTRICAL HEATING DEVICE

(75) Inventors: David Bikovsky, East Benjamin Ofra (IL); Dorith Bar-Adon, Jerusalem (IL)

(73) Assignee: HTTP-Hypothermia Therapy Ltd., Jerusalem (IL)

( * ) Notice: Subject to any disclaimer, the term of this patent is extended or adjusted under 35 U.S.C. 154(b) by 201 days.

(21) Appl. No.: 10/174,528

(22) Filed: Jun. 18, 2002

(65) Prior Publication Data

US 2003/0230565 A1 Dec. 18, 2003

(51) Int. Cl.$^7$ .............................................. H05B 3/34
(52) U.S. Cl. ........................................ 219/528; 219/545
(58) Field of Search ................................ 219/528, 527, 219/212, 543, 544, 549; 338/214, 299, 302, 303, 321

(56) References Cited

U.S. PATENT DOCUMENTS

| | | | | |
|---|---|---|---|---|
| 3,118,042 A | * | 1/1964 | Parker | 219/406 |
| 3,417,229 A | * | 12/1968 | Shomphe et al. | 219/528 |
| 3,805,023 A | * | 4/1974 | Wainer et al. | 219/543 |
| 4,245,149 A | * | 1/1981 | Fairlie | 219/528 |
| 4,532,410 A | | 7/1985 | Wehmeyer | |
| 4,752,672 A | * | 6/1988 | Grise | 219/543 |
| 4,908,497 A | * | 3/1990 | Hjortsberg | 219/539 |
| 4,912,306 A | * | 3/1990 | Grise et al. | 219/549 |
| 5,073,688 A | * | 12/1991 | McCormack | 219/212 |
| 6,153,856 A | * | 11/2000 | Lee | 219/212 |
| 6,297,770 B1 | * | 10/2001 | Ueda et al. | 342/357.12 |
| 6,300,597 B1 | * | 10/2001 | Lee | 219/212 |
| 6,664,512 B2 | * | 12/2003 | Horey et al. | 219/212 |

FOREIGN PATENT DOCUMENTS

| | | |
|---|---|---|
| DE | 29610436 | 12/1996 |
| EP | 0110121 | 6/1984 |
| GB | 811992 | 4/1959 |
| GB | 2104360 | 3/1983 |
| GB | 2207030 | 1/1989 |
| GB | 2316848 | 3/1998 |
| GB | 2360 922 A * | 10/2001 |
| JP | 722159 | 1/1995 |
| WO | 9709866 | 3/1997 |
| WO | 01/23659 | 4/2001 |
| WO | 0172249 | 10/2001 |

OTHER PUBLICATIONS

Derwent Abstract of DE 29610436 dated Dec. 19, 1996.
English Abstract of EP0110121 dated Jun. 13, 1984.
English Abstract of JP07022159 dated Jan. 24, 1995.

* cited by examiner

*Primary Examiner*—D. Pothier
*Assistant Examiner*—Vinod D. Patel
(74) *Attorney, Agent, or Firm*—Ladas & Parry (57) ABSTRACT

A heating unit is presented for use in a heating device for surface heating of a body to enable maintaining a required temperature of the body. The heating unit is composed of first and second elements each made of a material with a specific resistivity in a range of about 0.01–0.01 Ohm·mm$^2$/m, thereby enabling substantial flatness and flexibility of the heating unit. The first and second adjacent elements are accommodated in spaced-apart planes, are electrically insulated from each other, and have different resistance and different surface areas as compared to each other. The first element having the relatively high resistance and the relatively low surface area serves as a heater, and the second element, which is located closer to the body, when the heating unit is in the operation, serves as a distributor of heat created by the first element when connected to a power source. The heating unit is arranged such as to provide for compensating a magnetic field created by the heating unit when connected to the power source.

23 Claims, 3 Drawing Sheets

ELECTRICAL HEATING DEVICE

FIELD OF THE INVENTION

The present invention is generally in the field of heating techniques, and relates to an electrical heating unit and a heating device and system utilizing the same. The present invention is particularly useful for surface heating of a body, for example for heating a patient's body during surgical procedures and major operations.

BACKGROUND OF THE INVENTION

During a surgical procedure and within a certain time period thereafter, a patient's body requires to be externally heated. Heat transfer devices for transferring heat to the patient's body, which are used at present in operating rooms, are generally of two types: the first type utilizes a closed circuit with heated water circulating thereinside, and the second utilizes an open circuit, wherein heated air blows around the patient's body.

The heating technique of the first kind involves covering a patient with a thin rubber cover with warm water circulating through the cover. A device, equipped with a heat exchanger and pump, warms and circulates the water. Some of these devices also have the capability of regulating the temperature of the water based on core temperature measurement. These systems, however, give off heat to the environment and cause discomfort to the medical team. Moreover, these systems suffer from the following drawbacks: the very high cost of warming units, occasional leaking as the result of cutting the unit, blocking of the system when a patient is too heavy, and the system being bulky and heavy (containing about 3.5–5 liters of water).

As for the technique of the second type, it utilizes force air warming, forced air cooling and fluid warming technology. These systems can be mostly preset at one of three thermal levels up to 43° C. They have different configurations to fit the upper body, lower body, torso, and full body, as well as pediatric blankets. The warm air in the system escapes through the pores on the upper part of the blanket as well as through the flexible tubes into the theatre area, affecting the operating team and causing a certain degree of inconvenience. The energy suppliers can operate only one warming blanket at a time. Therefore, in most surgeries, either only the lower or the upper part of the body can be warmed by the system.

Intraoperative warming is needed during most operative procedures lasting longer than 30 minutes, and in all operations on children weighing less than 15 kilograms. The only situation where warming is practically not needed, are short procedures (less than 30 minutes), and when the temperature of the patient's body is intentionally lowered. Most patients begin losing body heat either prior to anesthesia or immediately upon the induction of anesthesia. Much body heat is lost within an hour of the start of anesthesia. Therefore, warming must begin either before or immediately following the induction of anesthesia.

One of the problems of intraoperative warming is associated with the requirement for servo-controlled delivery of heat, aimed at preventing overheating and allowing for the increased delivery of warmth to patients who are continuously losing body heat. Another problem is associated with the need for the circumferential warming of limbs, warming of discontinuous areas of the body and the possibility of warming sterile areas of the operative field. It is desirable to place a heating device on individual parts of the patient's body, and not underneath, so as to prevent the further loss of heat. Additionally, it is desirable to prevent the fan distribution of the warm air, and, while warming the desired parts of the patient's body, to prevent the warming of surgeons, nurses and anesthesiologists present at the time.

Electrical heating has evident advantages over the above techniques, such as the possibility of the continuous control of heating, including computer control and automatic management.

U.S. Pat. No. 4,532,410 discloses an electrical heating device for providing a feeling of warmth to the entire having body for comfort and protection in active outdoors pursuits in cold environments by means of conventional, convenient, practical and desirable materials such as a neck scarf. A heater is disposed in an appendage or bib attached to and made as an integral part of the neck scarf. The heater is composed of a heating element made of Nichrome sandwiched between two covering elements made of a heat diffusible material such as trincetate tape.

However, the use of electrical heating in operating rooms needs to guarantee the following three complex tasks:

1. It should guarantee electrical safety, namely, completely stave off the damage of the electrical voltage, especially taking into account that various solutions are in use during an operation, the presence of various metal instruments, the patient is undressed, as well as the possibility of hemorrhaging.

2. It should guarantee to avert the danger of burns that could be caused by the local overheating of heating elements.

3. It should guarantee the absence of the influence of the electromagnetic effects on electronic equipment involved in the operation or located in the vicinity of the heating device.

It is important to understand that in most cases, the above three tasks have to be accomplished together and completely. For example, to avoid the damage of electrical voltage, voltages as low as possible must be used. However, the use of low voltages with the required power compels the operation to take place with a high current, while this increase in current affects the electronics located in the vicinity of the heating device.

To decrease to zero the influence of the electromagnetic field of an electric power source onto the functioning electronics, it is known to utilize a bifilar arrangement of conductors. This technique is disclosed for example, in the patent document DE29610436. However, this technique unavoidably leads to local heating, owing to the fact that the conductors in which heat required for heating an object (e.g., a patient's body) is dissipated, are located very close to each other.

SUMMARY OF THE INVENTION

There is a need in the art to facilitate the technique of surface heating a body useful for heating a patient's body, by providing a novel electrical heating unit and heating device and system utilizing the same.

The present invention provides for electrical heating of the surface of a body with an as small as desired temperature gradient between the temperature of the heat-dissipating surface and the required temperature of the body, and provides for compensating a magnetic field created by the electrical heating unit in operation. A heating unit to satisfy these conditions can be fabricated from two elements, one made of a material with relatively high specific resistivity (e.g., stainless steel or transformer steel) and serving as a heater, and the other made from a material with relatively low specific resistivity (e.g. aluminum) serving as a heat-diffuser, thereby enabling using the elements in the form of short and wide strips, the fabrication method thereby being simple, with high accuracy of assembling. Such a heating unit is disclosed in WO 01/72249 assigned to the assignee of the present application. However, it appears that for various applications, for example, heating a patient's body, e.g., in an operating room, the heating until has to be flat and flexible and preferably also light.

According to the present invention, all the above conditions are achieved by making the heating unit from two functionally different adjacent elements electrically insulated from each other (e.g., each covered by a thin insulating layer, e.g., lacquer, or a laminating layer such as PVC, polypropylene, etc.) each being made from a metal foil with a low specific resistivity of about 0.015–0.1 Ohm·mm$^2$/m, such as aluminum, copper, iron, etc., the two elements having different resistance and different surface areas. That element, which is to be located closer to the body to be heated, has a relatively larger surface area and a relatively lower resistance as compared to the other element and serves as a distributor of heat created by the other element. In order to avoid local heating that could lead to burns, the surface of the heating unit through which heat is transferred to the body, i.e., the surface of the heat-distributor, should preferably be substantially equal to the surface area of the body parts to be heated. The operation of the heating unit thus provides for reducing the density of the heat flow that reaches the surface of the body to be heated and provides uniform heat transfer to the surface area to be heated.

There is thus provided according to one aspect of the present invention, a heating unit for use in a heating device for surface heating of a body to enable maintaining a required temperature of the body, the heating unit comprising the first and second elements each made of a material with a specific resistivity in a range of about 0.01–0.1 Ohm·mm$^2$/m thereby enabling substantial flatness and flexibility of the heating unit, the first and second adjacent elements being accommodated in spaced-apart planes, being electrically insulated from each other, and having different resistance and different surface areas as compared to each other, the first element having the relatively high resistance and relatively low surface area serving as a heater, and the second element, which is to be located closer to the body, when the heating unit is in operation, serving as a distributor of heat created by the first element when connected to a power source, the heating unit being arranged so as to provide for compensating a magnetic field created by the heating unit when connected to the power source.

The different resistance of the two elements can be achieved by making them of different geometries (i.e., shape and dimensions) and/or making them from different materials. For example, both the heater and the heat-distributor elements may be made of the same material (e.g., aluminum), wherein the heater is a flat strip folded in a serpentine- or ripple-like fashion and the heat-distributor is of a flat sheet-like geometry. In this case, in order to provide compensation of the magnetic field when only the heater element is connected to the power source, the heater strip is folded such that the length of each of the two adjacent substantially parallel segments of the strip is significantly larger than the length of the connecting segment between them. In another example, the heat distributor element and the heater have of a flat sheet-like geometry with the same perimeters, but the heater element is perforated (i.e., is made with holes) thereby having a relatively reduced effective cross-section. In this case, in order to reduce to zero the magnetic field created by the heating unit, the heat-distributor element is also connected to the power source such that the electric current in the two elements have the same magnitudes and opposite directions. The heater element and the heat-distributor element can be connected in series to the common power source. Generally, each of the two elements can be associated with its own power source. The power source may include an accumulator.

Thus, in one embodiment of the invention, the heat-distributor element is a flat flexible sheet (e.g., of a substantially rectangular shape) and is to be disconnected from the power source ("passive" heat distributor). In this case, the heater element is a flat strip folded in a serpentine- or ripple-like fashion with the length of two adjacent segments of the strip being significantly larger than that of the connecting segment between them.

According to another embodiment of the invention, the heat-distributor is also intended for connection to the power source ("active" heat distributor). In this case, the heat-distributor and the heater elements are shaped and connected to the power source such that the electric currents therein are of the same magnitudes and opposite directions, for example the heater and heat-distributor elements have the same perimeters and the heater element is formed with holes.

The heating unit may include an additional "passive" heat-distributor, in addition to the heater element and active heat-distributor element. This additional passive heat-distributor element is accommodated closer to the body to be heated, when the heating unit is in operation. For example, the "active" heat-distributor may be enclosed between the "passive" heat-distributor and the heater element.

As defined by accepted standards with respect to the specific application of maintaining the temperature of a patient's body under anesthesia, to completely avoid the damage of burns to a patient's body, the temperature on a heating unit itself, mainly on its external surface, should not exceed 41° C. At the same time, the surface temperature of the patient's body should not exceed 38° C. Accordingly, the heat flow from the heating element to the patient's body should be carried out with the maximum temperature gradient of 3° C. Taking into account that several layers of materials with very low heat conductivity (air, tissue, polyethylene) have to be accommodated between the heat dissipating element and the body, the exclusive complication of this problem is evident. The present invention solves this problem by providing the heat-distributor element and thereby reducing the temperature of the external surface of the heater element at 3–4° C., while maintaining the required temperature of the surface of the patient's body.

According to another aspect of the present invention, there is provided a heating device for surface heating of a body to enable maintaining a required temperature of the body, the heating device comprising an electrical heating unit and a power source for applying a required voltage to the heating unit, wherein:

said heating unit comprises first and second elements each made of a material with a specific resistivity in a range of about 0.01–0.1 Ohm·mm$^2$/m thereby enabling substantial flatness and flexibility of the heating unit, the first and second adjacent elements being accommodated in spaced-apart planes, being electrically insulated from each other, and having different resistance and different surface areas as compared to each other, the first element having the relatively high resistance and relatively low surface area serving as a heater, and the second element, which is to be located closer to the body, when the heating unit is in operation, serving as a distributor of heat created by the first element connected to the power source; and said heating unit is arranged so as to provide for compensating a magnetic field created by the heating unit when connected to the power source.

The heating unit of the present invention can operate with a substantially low voltage supply, e.g., 12V and less, in this case, the power source may comprise a step-down transformer interconnected between the power network and the heating device, and preferably also an accumulator unit, including for example at least two batteries, which are selectively operable by a switching unit, so as to connect a selective one of the batteries to the heating element. When one of the batteries is in operation, the other one may be charged with a charging unit.

The heating unit may be accommodated inside a bed-sheet for covering or wrapping the patient's body or body part to be heated, wherein such a cover or wrap may be made of any suitable material. The heating element may be formed of several separate parts for heating selective segments of the patient's body, such as legs, arms, torso, back or abdomen.

According to yet another aspect of the present invention, there is provided a heating system for heating a body up to a required temperature and maintaining this temperature, the system comprising a heating unit, a power source for supplying a required voltage to the heating unit, and a control unit wherein the heating unit comprises first and second elements each made of a material with a specific resistivity in a range of about 0.01–0.1 Ohm·mm$^2$/m, thereby enabling substantial flatness and flexibility of the heating unit, the first and second adjacent elements being accommodated in spaced-apart planes, being electrically insulated from each other, and having different resistance and different surface areas as compared to each other, the first element having the relatively high resistance and relatively low surface area serving as a heater, and the second element, which is to be located closer to the body, when the heating unit is in operation, serving as a distributor of heat created by the first element connected to the power source, the heating unit being arranged so as to provide for compensating a magnetic field created by the heating unit when connected to the power source; and the control unit connectable to the heating unit and operable to provide continuous control of the temperature of the body.

The control unit comprises a temperature sensor for measuring the core or body temperature, a processing and managing unit, and an indication unit, and is operable to provide continuous feedback loop control of the temperature of the body and of the operation of the temperature sensor, and to provide indication thereof.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF A PREFERRED EMBODIMENT

Figure 1:
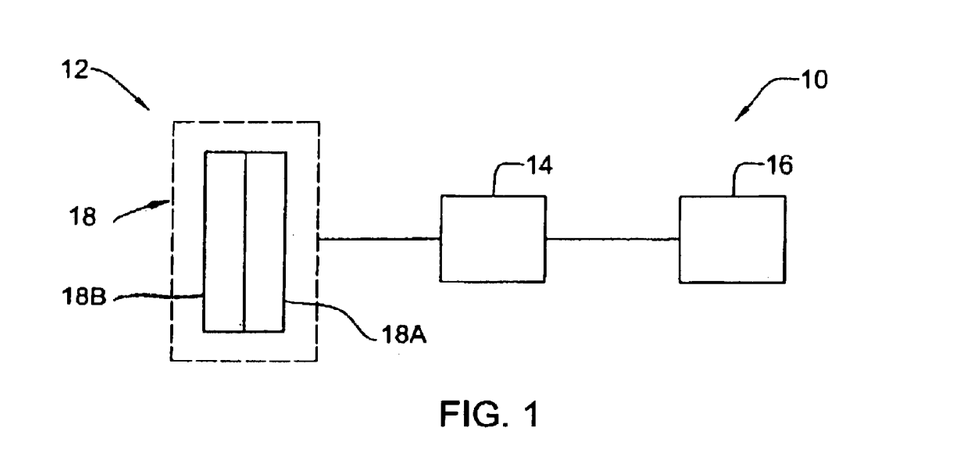
FIG. 1 is a block diagram of a heating system utilizing a heating unit according to the invention.

Referring to FIG. 1, there is illustrated a heating element 10 comprising a heating device 12 that includes a heating unit 18 according to the invention connectable to a power supply source 14; and a control unit 16. The construction of the control unit 16 does not form part of the present invention, and it may be of any known kind utilizing at least one temperature sensor, processors, contact and non-contact switches, etc. The power supply source 14 as a separate element is also known per se and therefore its construction and operation need not be specifically described, except to note that it operates to provide the normal operational mode of the heating unit 18 in accordance with instructions generated by the control unit 16.

The heating unit 18 is composed of two adjacent elements 18A and 18B accommodated in spaced-apart planes for example at a 1 mm distance between the elements. The elements 18A and 18B are electrically insulated from each other, for example, by lamination of at least the surfaces of the elements that face each other by insulating layers such PVC, polypropylene, etc. The elements 18A and 18B have different surface areas and different resistance: the element 18A, that is to be connected to the power source when the device is in operation and located farther away from the heated body, has relatively high resistance and relatively small surface area as compared to the element 18B, and serves as a heater element. The element 18B that is to be located closer to the body to be heated and may and may not be connected to the power source, serves as a distributor of heat created by the heater element 18A to provide a substantially homogeneous temperature field within the surface of the body. Preferably, the surface area of the heat-distributor element 18B by which it faces the body is of about the size of the surface of the body to be heated, and is preferably no less than 2 times larger than the heat dissipating surface of the element 18A. The heat distributor element 18B thus provides a "one-side" heat transfer (distribution) of the heat created by the element 18A. The elements 18A and 18B are made from the same or different materials with a specific resistivity in a range of about 0.01–0.1 Ohm·mm$^2$/m, e.g., aluminum, copper or iron foil. The heating unit 18 is thereby flat, flexible and light and can be located inside a bed-sheet (of any suitable material) for covering the patient's body or body part to be heated. Generally, the elements 18A and 18B are mounted with respect to each other so as to provide good thermal contact between them, namely such that there are substantially no heat losses within the contact area. When the heating unit 18 is put in operation, the element 18B is located between the element 18A and the body to be heated, and serves as a distributor of heat created by the heater element 18A.

Figure 2A:
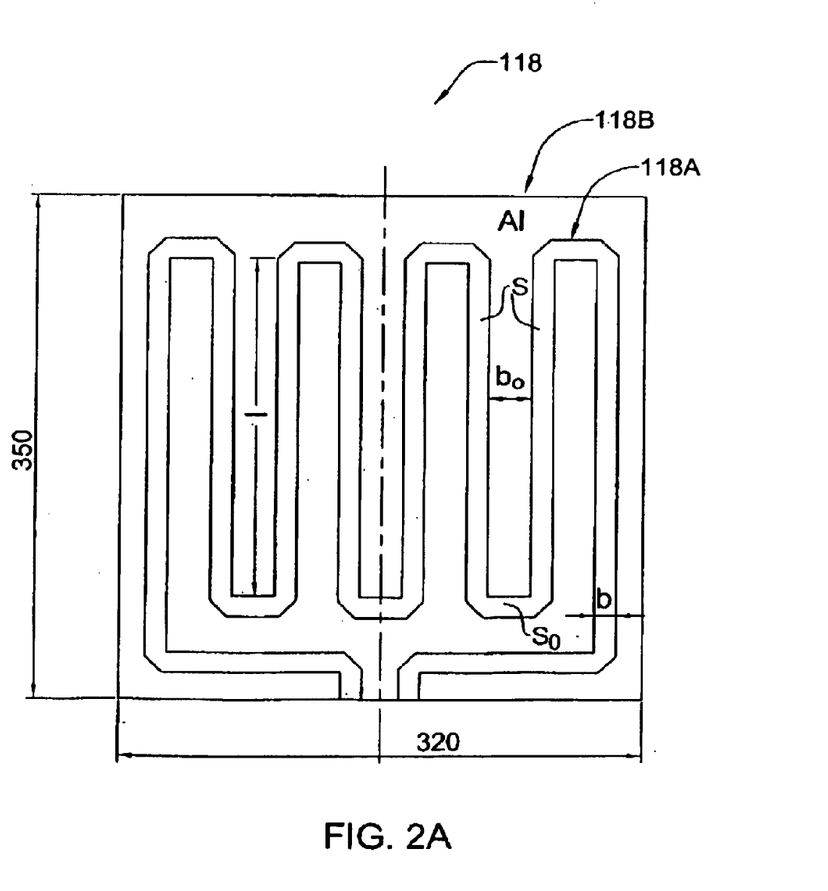
FIGS. 2A to 2C illustrate three example, respectively, of the heating unit suitable to be used in the system of FIG. 1.
Figure 2B:
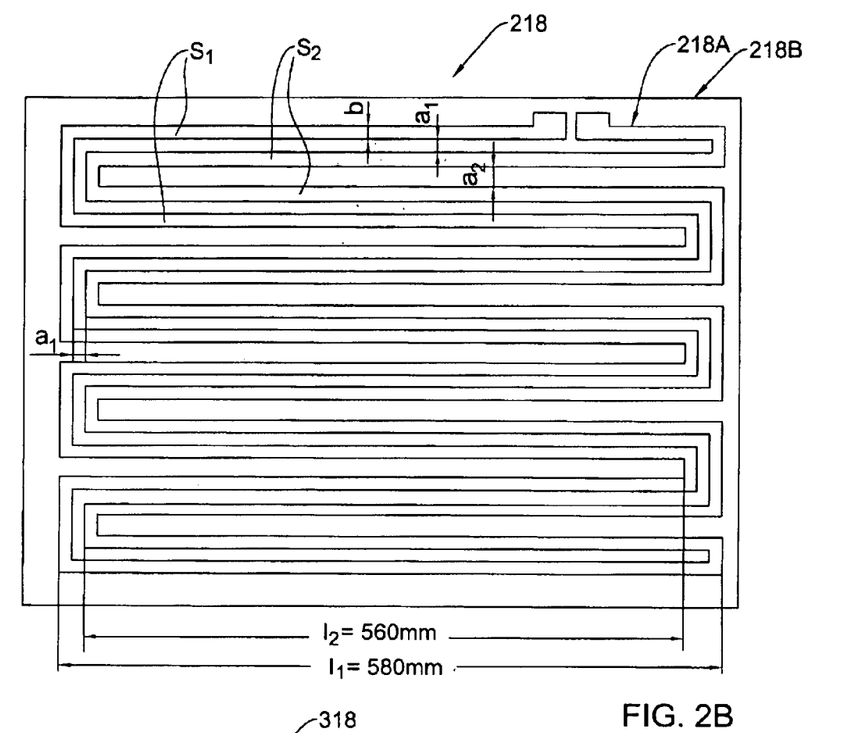
Figure 2C:
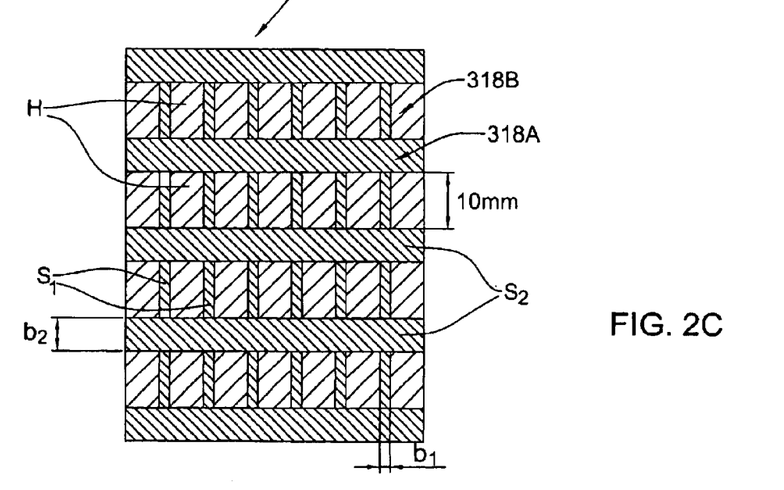

Reference is made to FIGS. 2A–2C showing three different examples, respectively, of the implementation of the heating unit according to the invention. In heating units 118 and 218 of FIGS. 2A and 2B, a "passive" heat distributor element is used (i.e., to be disconnected from the power source, when in the operation of the heating unit), while a heating unit 318 of FIG. 2C may utilize an "active" heat-distributor element.

Thus, the heating unit 118 (FIG. 2A) includes a heater element 118A in the form of a flat zigzag-like strip made of iron foil (ρ=0.1 Ohm×mm$^2$/m), and a heat-distributor element 118B that is a flat rectangular sheet made of aluminum foil (ρ=0.027 Ohm×mm$^2$/m) with the 350 mm×320 mm×0.018 mm dimensions. The strip 118A has a thickness δ=0.05 mm, width b=15 mm, and a total length L=2.6 m. In this specific example, the resistance of the strip 118A is 0.3 Ohm, and the 3V voltage supply thereto results in a current I=10 A and power P=30 W. The strip 118A is folded such that it defines several pairs of spaced-apart parallel segments, generally at S, of a length l=230 mm, wherein each two adjacent segments S are connected by a segment $S_0$ of the strip of a length $l_0$=25 mm (the ratio $l/l_0$ being 9.2). In other words, the strip is folded such that the length l of each of the spaced-apart substantially parallel segments S is substantially larger than the length $l_0$ of the strip segment $S_0$ between each two adjacent parallel segments. Hence, the arrangement of the strip 118A results in that electric currents flowing in the two adjacent segments S have equal magnitudes and opposite directions, and the fact that $l>>l_0$, results in the substantially zero magnetic field in the vicinity of the heating unit 118.

The heating unit 218 of FIG. 2B comprises a flat sheet-like heat-distributor element 218B made of aluminum foil of a thickness of 0.018 mm, and a flat serpentine-like strip 218A made of aluminum foil having a width b=10 m, thickness δ=0.018 mm, the total length L=9.77 m and resistance R=1.4 Ohm. The strip 218A is folded such that it defines a plurality of spaced-apart parallel identical segments $S_1$ (each of a length $l_1$=580 mm) and a plurality of spaced-apart parallel identical segments $S_2$ (each of a length $l_2$ 560 mm), with a space between the adjacent segments $S_1$ and $S_2$ being $a_1$=10 mm and a space between the two adjacent segments $S_2$ being $a_2$=23 mm. Thus, the elements 218A and 218B made of the same material have different geometries resulting in different resistance values, and the arrangement of the strip 218A provides for compensating the magnetic field created by the electric current passage therethrough. By supplying 5,1V to the heater element, a current I=3.5 A and power P=18 W are obtained.

Preferably, the dimensions of the heater element (e.g., strip) satisfy the following relationships:

$$l \geq k \cdot U_{heat} \cdot \sqrt{\frac{\delta}{\rho}} \qquad b \geq k \cdot I \cdot \sqrt{\frac{\rho}{\delta}}$$

Here, $U_{heat}$ is the voltage that falls on the heater element; I is the current flowing therethrough; ρ is the specific resistivity of the heater element material; δ is the thickness of the heater element; k is a coefficient depending on the body to be heated and the required temperature, selected so as to satisfy the condition that electric power supplied to the heater element is substantially equal to a heat power dissipated through the surface of the heater element. This approach for designing a heating element aimed at providing an as low desired temperature gradient between the temperature of the surface of the heating element and the required temperature of the body is developed by the inventor of the present application and disclosed in WO 97/09866. The main idea of this technique consists of considering the relationship between the physical parameters (i.e., length, width, thickness and specific resistivity) of the heating element, and its electrical parameters (i.e., voltage and current). The physical parameters are dictated by the heating power W required for heating a specific object to a desired temperature, i.e., W=kS, where S is the area of the outer surface of the heating element through which the heating power W is dissipated (i.e., product of the length l and width b of the outer surface), and k is the coefficient depending on the object to be heated and the desired temperature. The electrical parameters are dictated by electric power, W'-UI, supplied to the heating strip by a power source, wherein U is the electric potential and I is the electric current passing through the heating element, which depends on the specific resistivity ρ of the selected heating element material. To facilitate the understanding of this idea, let us assume that the temperature gradient needs to be reduced. For this purpose, the value of k is appropriately increased, which automatically causes the surface area S of the heating element to be increased. This, in turn, means that lower voltages should be supplied to the heating element, and this factor is used in selecting the electric conductive material with an appropriate specific resistivity.

In the example of FIG. 2C, the heating unit 318 is composed of heater and heat-distributor elements 318A and 318B made of the same material, e.g., aluminum, in the form of flat flexible sheets of equal perimeters. Here, however, the heater element 318B is formed with holes H (four spaced-apart arrays of holes in the present example) having the length of 10 mm and the width of 6 mm, defining aluminum segments $S_1$ and $S_2$ of dimensions $b_1$=3 mm and $b_2$=6 mm, respectively. The segments $S_1$ thus create the required resistance for the element 118A while the segments $S_2$ provides for better heat distribution (the so-called "internal heat distributors"). The heater element 318B thus has a relatively reduced effective cross-section defined by the width of the segments $S_1$ between the holes. When the heat-distributor element is also connected to the power source, the electric currents in the two elements have the same magnitude and opposite directions. This can be obtained by connecting the heater element and the heat-distributor element in series to the common power source and placing one on top of the other.

The provision of holes is associated with the following. Heat created by the heater element should be transferred to the heat-distributor element, which should distribute this heat within its entire surface so as to achieve a homogeneous temperature field within the heated surface. Since the distributor is to be very thin (to make the device flexible), even when using aluminum or copper as a heat-distributor material (high heat conductivity material) it would be difficult to transfer heat to high distances. For example, at a maximal thickness 0.014–0.018 mm of the heat-distributor, heat can be effectively transferred (maintaining the homogeneity of the temperature field within the heated surface) to a distance of up to 1 cm. Therefore, the distance between the projection of the active element dissipating heat (heater element) onto passive element distributing the heat (heat-distributor element) and any other location on the heat-distributor where the homogeneous temperature field is to be maintained should be up to 3–4 cm (preferably 2–3 cm). Hence, in order to provide the minimum of this distance when both the heater and the heat-distributor elements are flat sheets of substantially the same perimeter, the heater element is made with a plurality of holes such that the effective cross-section of the heater element provide the required resistance of the heater element to meet the requirements of power to be supplied to the heater element. By this, the entire surface of the heat-distributor is "filled" by the heat-element material, i.e., the maximal distance between the effective segments of the heater and distributor is reduced to the order of the hole's dimension (about 3–4 mm).

It should be noted although not specifically shown that both the heater element and the heat distributor element may be strips, e.g., folded in a ripple-like fashion, provided the heat-distributor element has a larger surface area than the heater element. Additionally, the heating unit may be composed of a heater element, an "active" heat-distributor (connected to the power source), and an additional "passive" heat-distributor element (disconnected from the power source) that is to be located closer to the body to be heated.

It should be noted that since the electric heating does not utilize liquid transfer or gaseous transfer at all, it is a simple task to divide the entire heating unit into several parts of equal dimensions and equal power, taking into account that the same power is required for heating both arms of a patient and his leg, in accordance with their dimensions. Therefore, each part of the heating unit may form a heater device with the power of 12 W, 6 W being needed for each patient's arm.

The present invention can be used to prevent and treat hypothermia and provide warmth to cold or shivering patients. In addition, the invention can be used whenever conditions exist that could cause patients to become cold/hypothermic. The invention can be used in operating rooms, recovery rooms, intensive care units, labor and delivery, emergency rooms, ships, aircrafts, long term care facilities, home health-care and other areas where a patient needs to be warmed by medical professionals. The invention can be used for heating surfaces of any size and body kind, in both humans and animals.

The power supply source (14 in FIG. 1) suitable to be used in the present invention may comprise an accumulator unit including two batteries, each selectively chargeable by a standard charging unit including a step-down transformer. Preferably, the power supply source activates the control unit and the heating unit and includes the first and second power supply units. For example, the first power supply provides a 6V voltage to the heating unit and the second power supply provides a 24V to the control unit. Additionally, each power supply charges two 6V batteries that activate the control unit and the heating unit when power out should occur. Each of the power supply units is adjusted to power that is required to recharge the batteries. The 6V power supply is adjusted to 7V DC and the 24V supply is adjusted to 27V DC. Since the power required for the heating unit is lower than the supplied power, a serial diode can be used that decreases the supplied power to the desired value. The power supply units may operate in a phase control manner. This technique is based on the principle of a component that operates as a switch. In this case, a SCR connected to the outlet of the entrance transformer reduces the power. The SCR is connected to a low AC power controlled by a control electronic card, which commands the SCR to start operation in a certain ignition angle dictating the outlet power. In case of low input power or over loading of the power supply, the control card commands the SCR to enlarge the ignition angle and by this, it corrects the power and returns the power to its original nominal value. Each power supply incorporates an internal shunt, which measures the current to protect the power supply against short-circuits or over loading. The shunt also performs current limitations.

The use of an accumulator as a power supply source eliminates the creation of an electromagnetic field, due to absence of the alternating current component. The accumulator provides direct voltage output in which the alternating component is absent, which results in the absence of electric current oscillations, and thereby the absence of the electromagnetic field. As for a magnetic field created by the electric current passing through the heater element, it can be reduced to zero as described above.

Figure 3:
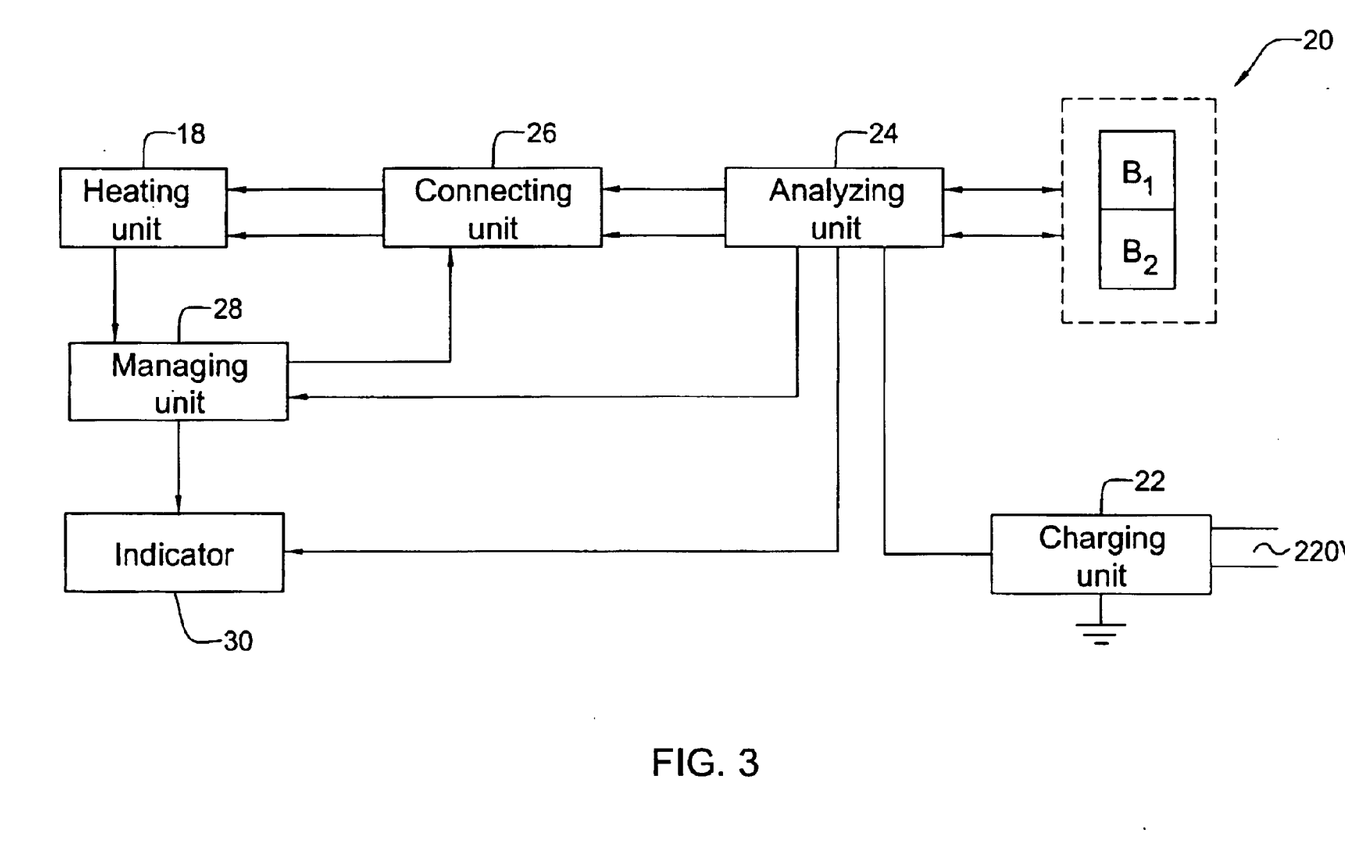
FIG. 3 is a schematic illustration of main functional components of the system of FIG. 1.

Reference is made to FIG. 3, exemplifying the functional elements of the system 10 of FIG. 1. The power supply source 14 utilizes an accumulator unit 20 including two batteries $B_1$ and $B_2$, each selectively chargeable by a standard charging unit 22 typically including a step-down transformer (not shown). The charging unit 22 is interconnected between a power network and an analyzing unit 24, which operates to switch between the batteries $B_1$ and $B_2$, so as to selectively connect one of them (which is charged) to the heating unit 18 (at least the heater element thereof). A connecting unit 26 operates to connect/disconnect the heating unit 18 to the accumulator unit 20. A processing and managing unit 28 is provided, being interconnected between the heating unit 18 and the connecting unit 26, and being connected to an indication unit 30.

The processing and managing unit 28 performs the following functions: it controls the operation of appropriately provided one or more temperature sensors (not shown) that generate data indicative of the current temperature of the patient's body; analyzes the current temperature of the patient's body; controls the operations of the switching and connecting units 24 and 26. The indication unit 30 provides indication of the operational state of the other unit, and the temperature of the patient's body.

When designing the above circuit, the following important operational requirements are considered; complete electrical safety for both the patient and medical personnel; continuous control of the temperature level of the patient's body; control of breaking of the temperature sensor circuit associated with means involved in the anesthesia process and with the external temperature sensors; continuous control of the extent of discharging of the battery with the possibility of switching to a reserve battery; reduction as much as possible in the signal-noise level with respect to other electronic equipment.

It should be noted that in the conventional systems of the kind specified, only the temperature of the patient's internal organs is determined. However, the temperature of the external surface of the patient's body in at least one location (but preferably 2 or 3 locations) on the body should be measured, since the disturbance of the vascular system may occur.

When putting the system of the present invention into operation, an indication that the system is connected to a power network is provided by any suitable means, for example, a lamp. Other suitable indicators, e.g., lamps, provide an indication that the fuses of the primary coil of the step-down transformer are in good condition. The voltage of 220V is supplied to the transformer, and the lowered alternating voltage of about 7V is provided on the secondary coil of the transformer. Alternating voltage is supplied from the secondary coil onto a diode bridge, and then onto a voltage stabilizer. As a result, an output DC voltage of about 6V is provided at the output of the charging unit 22. This voltage output is aimed at recharging the batteries, either battery $B_1$ or $B_2$, depending on the extent of the battery discharge.

As to which battery should be put in operation and which one should be recharged, this is determined by the analyzing scheme in the analyzing unit 24. During the analyzing procedure, the unit 24 generates a signal indicative of the switching procedure, in response to which a transistor (not shown) in the processing and managing unit 28 is closed, which means that the current flow in the heating strip is halted, and an electrical circuit between the units 24 and 26 is disconnected. This is implemented by mechanical means, such as relay contacts. This having been done, that battery which is more discharged among the two, is connected to the charging unit 22 by switches (relay contacts), while other battery is connected to the circuit line operating for heating. After the completeness of the process of switching between the batteries, control signals are sequentially generated in the processing and managing unit 28, so as to put the heating device into operation, namely, the relay contacts are closed and the transistor in the unit 28 it completely opened. Then, the unit 28 is completely put in operation.

As indicated above, the presence of the temperature sensors is considered. The processing and managing unit 28 continuously controls the magnitude of the temperature and controls situation of accidentally breaking the temperature sensors. Concurrently with this control, the indication unit 30 proves information about the temperature value exposed to an authorized person.

Following are several processes that may occur during the operation in an operating room:

1. The temperature of the patient's body exceeds the given value. In this case, a corresponding signal is generated in the processing and managing unit 28, so as to lock the transistor. Accordingly, the relay contacts are disconnected. The indication unit 30 provides a signal indicative of the fact that the heating process is halted. The unit 28 continues to control the decrease in the temperature of the patient's body, and upon detecting that the temperature is less that the defined threshold, generates corresponding signals so as to switch on the heating process (the relay contacts are closed and the transistor is opened). The indication unit 30 provides indication to the fact that the heating is turned on.

2. The temperature of the patient's body does not reach the given value, and an indication signal indicative of switching between the batteries is generated by the unit 30. In this case, the processing and managing unit 28 generates a sequence of signals aimed at disconnecting the heating unit 18 from the battery, and operates the analyzing unit 24 for switching between the batteries. The units 24 and 28 operate together so as to allow the switching process. After switching to the correct battery, the heating unit is supplied with the required voltage so as to perform the heating process.

In the present example, the electrical conditions are as follows:

Electric voltage of about 220V is supplied to the accumulator unit 22 through screened wires with doubled electrical insulation. The fuses are mounted in two phases of the primary network of the transformer. Human access to the fuses without the use of a special tool is completely avoided. The transformer is of a down step torroidal kind, and the strengthened double insulation is provided between its primary and secondary windings and between the primary winding of the magnetic core. There is no such moment in time when the heating unit is in its operating position during the switching between the batteries. In other words, when the processing and managing unit 28 operates to provide switching between the batteries, the heating unit 18 is previously disconnected and maintained in this position during the entire re-switching process, i.e., the heating unit is mechanically (and electrically) disconnected from the accumulator unit 20 and from the charging unit 22. Thus, only one, charged battery is always electrically connected to the heating unit, while being at that time disconnected from the charging unit 22 (i.e., from the power network).

It should be noted that the present invention can generally be used with a power source of any suitable kind, and is not limited to the above examples.

Thus, the present invention provides a flat and flexible heating unit that enables an as low as desired temperature gradient between the temperature of the surface of the heat dissipating surface in the heating unit and that of a body to be heated, and reduction to zero of a magnetic field created by the heating unit when in operation. The provision of the heat-distributor element enables to provide the uniform distribution of heat flow directed towards the body (homogeneous temperature field within the heated body surface), and to reduce the heat flow reaching the body.

Those skilled in the art will readily appreciate that various modifications and changes can be applied to the preferred embodiment of the invention as hereinbefore exemplified without departing from its scope defined in and by the appended claims.

What is claimed is:

1. A heating unit for use in a heating device for surface heating of a body to enable maintaining a required temperature of the body, the heating unit comprising first and second elements each made of a material with a specific resistivity in a range of about 0.01–0.1 Ohm·mm$^2$/m thereby enabling substantial flatness and flexibility of the heating unit, the first and second adjacent elements being accommodated in spaced-apart planes, being electrically insulated from each other, and having different resistance and different surface areas as compared to each other the first element having the relatively high resistance and relatively low surface area serving as a heater, and the second element which is to be located closer to the body, when the heating unit is in operation, serving as a distributor of heat created by the first element when connected to a power source, the heating unit being arranged so as to provide for compensating a magnetic field created by the heating unit when connected to the power source.

2. The heating unit according to claim 1, wherein the surface area of the second element is at least two times higher than the surface area of the heater element.

3. The heating unit according to claim 1, wherein the external surface area of the second element is substantially equal to the surface of the body to be heated.

4. The heating unit according to claim 1, wherein the first and second elements are made of the same material.

5. The heating unit according to claim 1, wherein the first and second elements are made of different materials.

6. The heating unit according to claim 1, wherein the first element is made of one of the following materials: aluminum, copper, iron.

7. The heating unit according to claim 1, wherein the second element is made of aluminum or copper.

8. The heating unit according to claim 1, wherein the arrangement of the heating unit providing for compensating the magnetic field is such that the first element, which is to be connected to the power source is a strip folded in a ripple-like fashion and having a length of each of two adjacent segments of the strip significantly larger than a length of a connecting segment between them, and the second element which is to be disconnected from the power source during the operation of the heating unit has a flat sheet-like geometry.

9. The heating unit according to claim 1, wherein the first and second elements have flat sheet-like geometries of substantially equal perimeters, and the first element is formed with a plurality of holes.

10. The heating unit according to claim 1, wherein the first and second elements, when both connected to the power source, are characterized by electric currents of the same magnitude and opposite directions, thereby resulting in the compensation of magnetic fields created by the electric currents passage through the elements.

11. The heating unit according to claim 1, wherein the length, l, and width, h, of the first element satisfy the following relationships:

$$l \geq k \cdot U \cdot \sqrt{\frac{\delta}{\rho}} \qquad b \geq k \cdot I \cdot \sqrt{\frac{\rho}{\delta}}$$

wherein U is the voltage that falls on the first element; I is the current flowing through the first element; ρ is the specific resistivity of the first element material; δ is the thickness of the first element; k is a coefficient depending on the body to be heated and said required temperature so as to satisfy the condition that electric power supplied to the heating unit is substantially equal with a heat power dissipated through the surface of the first element.

12. The heating unit according to claim 1, at least adjacent surfaces of the first and second elements are coated with thin insulating layers.

13. A heating device for surface heating of a body to enable maintaining a required temperature of the body, the heating device comprising the heating unit of claim 1, and a power source for supplying a required voltage to the heating unit.

14. A heating device for surface heating of a body to enable maintaining a required temperature of the body, the heating device comprising an electrical heating unit and a power source for supplying a required voltage to the heating unit, wherein:

said heating unit comprises first and second element each made of a material with a specific resistivity in a range of about 0.01–0.1 Ohm·mm²/m thereby enabling substantial flatness and flexibility of the heating unit, the first and second adjacent elements being accommodated in spaced-apart planes, being electrically insulated from each other, and having different resistance and different surface areas as compared to each other, the first element having the relatively high resistance and relatively low surface area serving as a heater, and the second element, which is to be located closer to the body, when the heating unit is in operation, serving as a distributor of heat created by the first element connected to the power source; and said heating unit is arranged so as to provide for compensating a magnetic field created by the heating unit when connected to the power source.

15. The device according to claim 14, wherein said required voltage being substantially low, of about 12V or less.

16. The device according to claim 14, wherein said power source comprises an accumulator unit.

17. The device according to claim 16, wherein said accumulator unit comprises at least two batteries, selectively operable by a switching unit, so as to connect a selective one of the batteries to the heating unit.

18. The device according to claim 17, wherein a charging unit is provided and selectively operable to charge that one of the batteries which is disconnected from the heating unit.

19. The device according to claim 17, wherein said selected one of the batteries, while being connected to the heating unit, is mechanically and electrically disconnected from a power network.

20. The device according to claim 14, wherein said heating unit is accommodated inside a bed-sheet for covering or wrapping the body to be heated.

21. A heating system for heating a body up to a required temperature and maintaining this temperature, the system comprising the heating device of claim 14 and a control unit.

22. A heating system for heating a body up to a required temperature and maintaining this temperature, the system comprising a heating unit, a power source for supplying a required voltage to the heating unit, and a control unit, wherein the heating unit comprises first and second elements each made of a material with a specific resistivity in a range of about 0.01–0.1 Ohm·mm²/m thereby enabling substantial flatness and flexibility of the heating unit, the first and second adjacent elements being accommodated in spaced-apart planes, being electrically insulated from each other, and having different resistance and different surface areas as compared to each other, the first element having the relatively high resistance and relatively low surface area serving as a heater, and the second element, which is to be located closer to the body, when the heating unit is in operation, serving as a distributor of heat created by the first element connected to the power source, the heating unit being arranged so as to provide for compensating a magnetic field created by the heating unit when connected to the power source; and the control unit connectable to the heating unit and operable to provide continuous control of the temperature of the body.

23. The system according to claim 22, wherein said control unit comprises a temperature sensor for measuring the core or body temperature, a processing and managing unit, and an indication unit, and is operable to provide continuous feedback loop control of the temperature of the body and of the operation of the temperature sensor, and to provide indication thereof.

* * * * *